United States Patent [19]

Chang et al.

[11] Patent Number: 5,294,438

[45] Date of Patent: Mar. 15, 1994

[54] LUBRICATING AND MOISTURIZING SHAVING PREPARATIONS

[75] Inventors: Robert W. H. Chang, Roseville; Wayne K. Dunshee, Maplewood; Jeffrey F. Andrews, Stillwater, all of Minn.

[73] Assignee: Minnesota Mining and Manufacturing Company, St. Paul, Minn.

[21] Appl. No.: 867,574

[22] Filed: Apr. 13, 1992

Related U.S. Application Data

[63] Continuation of Ser. No. 651,330, Feb. 5, 1991, abandoned.

[51] Int. Cl.$^5$ .......................... A61K 7/06; A61K 9/107
[52] U.S. Cl. .......................... 424/73; 424/45; 424/47; 424/401; 424/78.03; 514/945; 514/938
[58] Field of Search ............... 424/73, 45, 47, 401, 424/78.03

[56] References Cited

U.S. PATENT DOCUMENTS

| | | | |
|---|---|---|---|
| 1,709,460 | 4/1929 | Casean | 424/45 |
| 4,145,411 | 3/1979 | Mende | 424/47 |
| 4,381,293 | 4/1983 | Michel | 424/401 |
| 4,495,169 | 1/1985 | Schmolka | 424/47 |
| 4,659,573 | 4/1987 | Frischling et al. | 424/63 |
| 4,661,104 | 4/1987 | von Bittera et al. | 424/83 |
| 4,902,503 | 2/1990 | Umemura et al. | 424/83 |
| 4,963,351 | 10/1990 | Weston | 424/73 |
| 4,999,183 | 3/1991 | Mackles | 424/73 |

FOREIGN PATENT DOCUMENTS 869966 5/1971 Canada.

OTHER PUBLICATIONS

Cosmetics and Toiletries (1985), vol. 100, pp. 83–89.
Balsam et al. (1972), Cosmetics: Science and Technology, vol. 2, Chapters 16, and 17 Wiley-Interscience.

*Primary Examiner*—Thurman K. Page
*Assistant Examiner*—Raji Bawa
*Attorney, Agent, or Firm*—Gary L. Griswold; Walter N. Kirn; Dale A. Bjorkman

[57] ABSTRACT

The lubricity of any shaving preparation is enhanced by providing an emollient oil and a thermoplastic polymeric elastomer additive in an amount effective to increase its lubricity. Specific shaving preparations suitable for application to human or animal skin may comprise at least 5% by weight of an emollient oil, and a thermoplastic polymeric elastomer additive in a ratio of emollient oil to additive of between about 5:1 and 20:1, and preferably in a ratio of between about 8:1 and 10:1. Shaving creams generally contain 5–30% of an emollient oil, a thermoplastic polymeric elastomer additive present in a ratio of emollient oil to additive of between about 5:1 and 20:1, and at least 5% by weight of soap, detergent or a combination thereof.

18 Claims, No Drawings

LUBRICATING AND MOISTURIZING SHAVING PREPARATIONS

This is a continuation of application Ser. No. 07/651,330 filed Feb. 5, 1991, now abandoned.

FIELD OF THE INVENTION

This invention relates to shaving preparations.

BACKGROUND ART

Razor and blade shaving preparations are provided in the art to lubricate the skin to allow the blade to glide easily over the skin and minimize irritation. These preparations also soften the hair and hold the hairs erect to facilitate cutting. Shaving preparations typically incorporate a fatty acid soap, a gelling and/or foaming agent, a lubricating agent, appropriate surfactants and other additives such as humectants, oils, preservatives, colorants and fragrances. Other formulations include "shaving assisting compositions" incorporating high amounts of emollient oils, silicones or alcoholic lotions. These compositions may be used as a prelubricant in conjunction with a conventional soap shaving formulation, or may be used alone and applied directly to the skin or the shaving blade.

Although a number of products are currently available which cater to the needs of those with sensitive skin, better formulations are highly sought after for improving the lubricity of such compositions and providing adequate moisturization of the skin.

SUMMARY OF THE INVENTION

The present invention provides a method of enhancing the lubricity of any shaving preparation by providing an emollient oil and a thermoplastic polymeric elastomer additive in an amount effective to increase its lubricity.

Specific shaving preparations suitable for application to human or animal skin may comprise at least 5% by weight of an emollient oil, and a thermoplastic polymeric elastomer additive in a ratio of emollient oil to additive of between about 5:1 and 20:1, and preferably in a ratio of between about 8:1 and 10:1.

Preferably, the present invention provides a shaving cream preparation comprising five to thirty percent of an emollient oil, a thermoplastic polymeric elastomer additive in a ratio of emollient oil to additive of between about 5:1 and 20:1, and preferably in a ratio of between about 8:1 and 10:1, and at least 5% by weight of soap, detergent or a combination thereof.

The term emollient oil as used herein refers to any cosmetically acceptable oil or mixture of oils which forms a barrier on the skin capable of retarding the evaporation of water.

A thermoplastic polymeric elastomer additive is a block copolymer material having an elastomeric block and a thermoplastic block, wherein the polymer softens and flows under shear when heated, but recovers its strength and elastomeric properties on cooling.

The compositions of the present invention provide superior lubricating properties as compared to the prior art shaving preparations. The presence of the thermoplastic polymeric elastomer additive significantly enhances the moisturizing and lubricating effect of the ultimate composition. Users also experience an excellent post shaving softness feel that could be described as "silky." Because the user can apply more pressure on the razor, a closer shave can be achieved with less irritation than conventional shaving preparations. Shaving preparations according to the present invention therefor have particular value for those having especially sensitive skin.

Unless otherwise noted, all ratios and percentages provided herein are by weight.

DETAILED DESCRIPTION OF THE PRESENTLY PREFERRED EMBODIMENTS

The thermoplastic polymeric elastomer additive is typically selected from one or more block copolymer rubbers, and preferably from synthetic rubbers. The preferred rubbers are di-block or tri-block copolymers having an elastomeric block and a thermoplastic block. Most preferably, the rubbers to be used in the present invention are the tri-block A-B-A type copolymers with the elastomeric block in the center and thermoplastic block on each end. The thermoplastic block is provided by a component having a hard character, such as styrene. Thermoplastic blocks typically are made from monomers wherein the corresponding homopolymer has a $T_g$ greater than about 90° C. The elastomeric block is preferably selected from butadiene, isoprene, ethylene/butylene, polyisobutylene or the like. Elastomeric blocks are typically made from monomers wherein the corresponding homopolymer has a $T_g$ less than about 10° C. The thermoplastic block of the polymer preferably constitutes between about 15–40% by weight of the total polymer. Most preferably, the additives are selected from the Kraton ® thermoplastic rubber polymers available from Shell Oil Co., Houston, Tex.

The emollient oil is preferably selected from any of the light oils used in the cosmetic art as emollients. Examples of such oils include isopropyl myristate, isopropyl palmitate, mineral oil, vegetable oils, seed oils, lanolin derivatives, and fatty acid glycerides. Other examples include fatty acids, liquid water soluble polyols, glycerin, propylene glycol, sorbitol, polyethylene glycol, ethoxylated/propoxylated ethers of methyl glucose (e.g., methyl gluceth-20, commercially available from Amerchol, Inc., Edison, N.J.) and ethoxylated/propoxylated ethers of lanolin alcohol (e.g., Solulan-75, commercially available from Amerchol, Inc., Edison, N.J.).

Preferred shaving preparations of this invention are shaving cream formulations comprising a soap or detergent. To provide sufficient lather, such shaving cream formulations generally comprise at least 5% by weight of a soap or detergent or combination thereof. Preferably, the shaving cream formulation comprises between 10 and 50%, and more preferably between 15 and 30% soap or detergent or combination thereof. In addition to the soap and/or detergent component, such ingredients as humectants, perfumes, colorants, preservatives, foam boosters, stabilizers, bacteriostats, cooling agents, pilomotor agents, propellants, and appropriate surfactants and emulsifiers should be incorporated as necessary to provide a pleasing shaving cream composition. The basic preparative techniques and approaches to select ingredients for a shaving cream formulation other than the oil/elastomer additive component are well known to those skilled in the shaving cream art. Reference may be had to Harry's Cosmeticology, Seventh Edition, 1982, for basic background information in this subject matter.

A typical soap to be used in this composition is a water-soluble soap formed from an alkanolamine and/or alkali salt with a higher fatty acid, vegetable oils, seed oils, or animal fats. A higher fatty acid is one which contains 10 to 18 carbon atoms, and examples include myristic acid, oleic acid, palmitic acid, and stearic acid. The preferred soap is a mixture of potassium stearate and triethanolammonium stearate formed in situ by the addition of neutralizing bases to stearic acid in aqueous medium. Other mixtures of stearates, such as 1:5 sodium and potassium stearate are also preferred. Normally, the bases are added in an amount sufficient to leave about 3% free fatty acid. It is also appropriate, in the case of stearic acid soaps, to add coconut oil fatty acid at a ratio of about 3:1 stearic acid/coconut oil to increase lather.

In the shaving cream art, some soap and detergent compositions are not generally used because they are viewed to be too drying to the skin. Because the present invention provides shaving formulations that have excellent moisturizing properties, detergent compositions not previously thought to be appropriate for use in shaving cream formulations may be acceptable for application to skin. Thus, even compositions primarily comprising anionic soaps or surfactants that incorporate an emollient oil and a thermoplastic polymeric elastomer additive in an effective amount may provide satisfactory lubrication and moisturizing properties.

A humectant may be added to the formulation to prevent the foam from rapidly drying and collapsing. Suitable humectants include propylene glycol, sorbitol, glycerol, and hydrogenated starch hydrolysate.

Surfactants include fatty acid esters such as polyethylene glycol monostearate or glyceryl monostearate, sorbitan monolaurate, polyoxyethylene 40 stearate, fatty acid soaps such as sodium lauryl sulfate, sodium lauryl ether sulfate, and triethanolamine lauryl sulfate.

Shaving preparations according to this invention may be provided in any form appropriate for delivering a shaving preparation to the skin to be shaved. For example, the preparation may be a lather shaving stick, an aerosol shaving foam, a post-foaming gel or a brushless or non-lathering cream.

The following examples serve to further illustrate the invention and should in no way be construed to be limiting the invention to these examples. All percentages listed are by weight.

EXAMPLE 1

| Ingredient | % Weight |
|---|---|
| Elastomer/emollient | |
| isopropyl myristate NF | 13.50 |
| Kraton ® 1107 | 1.5 |
| Water Phase Components | |
| deionized water | 63.98 |
| methyl paraben USP | 0.10 |
| propyl paraben USP | 0.05 |
| potassium hydroxide USP | 0.12 |
| triethanolamine | 0.75 |
| propylene glycol | 8.00 |
| polysorbate 60 | 1.00 |
| Oil Phase Components | |
| propylene glycol monostearate | 3.50 |
| stearic acid USP | 6.00 |
| dimethyl cocoamine oxide | 0.50 |
| coconut oil diethanolamide | 0.50 |
| sorbitan monostearate | 0.50 |

The preparation of all of the shaving cream formulations given in the examples is the same and is as follows:

1. Heat the Kraton ® 1107 in the isopropyl myristate at 190°-200° C. until all of the Kraton ® 1107 is dissolved in the isopropyl myristate.
2. Heat the water phase ingredients to 170°-180° F. and stir constantly until all of the solids are dissolved.
3. In a separate container, heat the oil phase components together with the Kraton ® 1107/isopropyl myristate solution at 170°-180° F. until a clear solution is formed.
4. Maintaining the temperature at 170°-180° F., slowly add the oil phase liquid to the water phase liquid with constant stirring. Mix for another 30 minutes at 170°-180° F. Cool mixture to room temperature with constant stirring.
5. An aerosol cream can be made by adding a suitable propellant. Propellants including hydrocarbon mixtures of isobutane and propane are acceptable. The desired vapor pressure for the aerosol is obtained by adjusting the proportions of the said hydrocarbons. In the preferred embodiment, the aerosol cream is made by adding 3% by weight of a mixture of 80% isobutane and 20% propane having a vapor pressure of 46 psi.

EXAMPLE 2

| Ingredient | % Weight |
|---|---|
| Elastomer/Oil Emollient Components | |
| Kraton ® 1107 | 1.50 |
| isopropyl myristate | 13.50 |
| Water Phase Components | |
| deionized water | 66.13 |
| triethanolamine | 0.25 |
| potassium hydroxide USP | 0.12 |
| propylene glycol | 8.00 |
| Oil Phase Components | |
| polyethylene glycol monostearate | 3.50 |
| stearic acid USP | 4.00 |
| dimethyl cocoamine oxide | 0.50 |
| coconut oil diethanolamide | 0.50 |
| white beeswax | 2.00 |

EXAMPLE 3

| Ingredient | % Weight |
|---|---|
| Elastomer/Emollient Components | |
| Kraton ® 1107 | 2.00 |
| isopropyl myristate | 18.00 |
| Water Phase Components | |
| deionized water | 62.30 |
| propylene glycol | 5.00 |
| Carbopol ™ 941[1] | 0.20 |
| Tween ™ 20[1] | 1.00 |
| triethanolamine | 1.00 |
| Oil Phase Components | |
| polyethylene glycol monostearate | 3.00 |
| stearic acid USP | 6.00 |
| coconut oil diethanolamide | 0.50 |
| cetyl alcohol | 1.00 |

[1]Carbopol ™ and Tween 20 are surfactants commercially available from B. F. Goodrich, Cleveland OH, and ICI Americas, Inc., Wilmington DE, respectively.

EXAMPLE 4

| Ingredient | % Weight |
|---|---|
| Elastomer/Emollient Components | |
| Kraton ® 1107 | 2.50 |

| Ingredient | % Weight |
| --- | --- |
| isopropyl myristate | 22.50 |
| Water Phase Components | |
| deionized water | 53.35 |
| methyl paraben | 0.10 |
| propyl paraben | 0.05 |
| glycerin | 5.00 |
| triethanolamine | 2.00 |
| Oil Phase Components | |
| polyethylene glycol monostearate | 4.00 |
| stearic acid USP | 6.00 |
| coconut oil diethanolamide | 1.00 |
| Myrj TM 52[1] | 1.00 |
| sodium lauryl ether sulfate | 0.50 |
| Solulan TM 97[1] | 2.00 |

[1]Myrj TM and Solulan TM 97 are surfactants commercially available from ICI Americas, Inc., Wilmington DE, and Amerchol, Edison NJ, respectively.

EXAMPLE 5

| Ingredient | % Weight |
| --- | --- |
| Elastomer/Emollient Components | |
| Kraton ® 1107 | 2.00 |
| isopropyl myristate | 18.00 |
| Water Phase Components | |
| deionized water | 60.50 |
| Polyox TM WSRN 80[1] | 1.00 |
| sorbitol (70% in water solution) | 5.00 |
| triethanolamine | 1.00 |
| Oil Phase Components | |
| polyethylene glycol monostearate | 3.00 |
| stearic acid USP | 6.00 |
| coconut oil diethanolamide | 1.00 |
| dimethyl cocoamine oxide | 1.00 |
| Tween TM 20[1] | 1.00 |
| cetyl alcohol NF | 1.00 |

[1]Polyox TM WSRN 80 and Tween TM 20 are surfactants commercially available from Union Carbide Corp., New York NY and ICI Americas, Inc., Wilmington DE, respectively.

EXAMPLE 6

This is a formulation for a brushless shaving cream.

| Ingredient | % Weight |
| --- | --- |
| Elastomer/Emollient Components | |
| Kraton ® 1107 | 2.00 |
| isoporpyl myristate | 18.00 |
| Water Phase Components | |
| deionized water | 50.85 |
| methyl paraben | 0.10 |
| propyl paraben | 0.05 |
| triethanolamine | 1.00 |
| Oil Phase Components | |
| stearic acid USP | 20.00 |
| stearyl alcohol NF | 2.00 |
| cetyl alcohol | 2.00 |
| sodium lauryl ether sulfate | 2.00 |
| Solulan TM 97[1] | 2.00 |

[1]Solulan TM 97 is a surfactant commercially available from Amerchol, Edison NJ.

EXAMPLE 7

| Ingredient | % Weight |
| --- | --- |
| Elastomer/Emollient Components | |
| Kraton ® 1107 | 1.00 |
| isopropyl myristate | 9.00 |
| Water Phase Components | |
| deionized water | 66.89 |
| methyl paraben | 0.10 |
| propyl paraben | 0.10 |
| potassium hydroxide | .10 |
| triethanolamine | .40 |
| sorbitol (70% solution in water) | 10.00 |
| Oil Phase Components | |
| stearic acid USP | 5.00 |
| myristic acid | 2.50 |
| stearyl alcohol | 0.50 |
| Arlacel TM 165[1] | 0.50 |
| Tween TM 80[1] | 2.00 |
| Varox TM 375[1] | 1.00 |
| Stepanol TM WA paste[1] | 1.00 |

[1]Arlacel TM 165, Tween TM 80, Varox TM 375 and Stepanol TM WA paste are surfactants commercially available from ICI Americas, Inc. (first two listed surfactants), Wilmington DE; Sherex Chemical Co., Inc., Dublin, OH; and Stepan Company, Northfield, IL, respectively.

Example 7 was prepared as specified in Example 1 except that after cooling, 2.65 grams of isopropanol were added per 100 grams of shaving cream base before filling the cans with cream and propellant. This enhanced the foaming so that a copious foam formed immediately from the nozzle.

THE INCLINED PLANE SLIPPERINESS TEST

Shaving formulations according the present invention enjoy a greater lubricity as compared to compositions not containing the oil/elastomer additive component. This increased lubricity is demonstrated by the Inclined Plane Slipperiness Test.

The slipperiness of a composition is measured in this test by quantitatively measuring the angle of a sliding plane at which a 500 gram weight in an aluminum dish slides down the track of the slippery material on a steel panel. The panel is a 4 inch×8 inch×0.012 inch thick polished, tin coated steel panel obtained from Ball Corporation, Metal Decorating & Service Division, 400 West 42nd Place, Chicago, Ill. 60632. The aluminum dish is a polished standard 57 mm aluminum weighing dish available from the Fisher Scientific Catalog number 8-732.

The test is conducted as follows:
1. A thin layer of oil or a shaving cream thickness of at least one mm is spread along the length of the panel.
2. A 500 gram weight in a 57 mm aluminum weighing dish is placed on one end of the panel laying on a flat surface.
3. The end of the panel with the weight is slowly and carefully raised to make an inclined plane.
4. The operator stops lifting the panel immediately when the dish starts to slide down the plane and the angle of the inclined plane is recorded. This angle is the Inclined Plane Slipperiness Test Angle.

It will be appreciated that the exact angle observed may differ from one dish and plane to another, depending on the polish of the surfaces and other experimental factors that differ from lab to lab. Regardless of the empirical comparison from one test facility to another, the relative slipperiness of different compositions is well predicted by this method, and comparative measurements may be satisfactorily accomplished.

Table I demonstrates the effect of increased lubricity achieved by adding an elastomeric additive that is a Kraton ® rubber to an emollient oil alone. Even amounts as low as 2% of elastomeric additive significantly increase the lubricity of the oil. This demonstration shows that adding an elastomeric additive to many different types of oils results in increased lubricity in all occurrences.

Preferably, the shaving preparation of this invention has an Inclined Plane Slipperiness Test Angle that is less than about 70% of the Inclined Plane Slipperiness Test Angle of the same composition not containing thermoplastic polymeric elastomer additive.

TABLE I

INCLINED PLANE SLIPPERINESS TEST OF OIL LIQUIDS

| MATERIAL | ANGLE IN DEGREES |
|---|---|
| 1. Isopropyl myristate | 12 |
| Isopropyl myristate + 10% Kraton ® 1107 | 5 |
| Isopropyl myristate + 10% Kraton ® 1101 | 5 |
| 2. Unimate ™ 600 | 11 |
| Unimate ™ 600 + 10% Kraton ® 1107 | 3 |
| 3. Oleic Acid | 7 |
| Oleic Acid + 10% Kraton ® 1107 | 5 |
| 4. Oleol Alcohol | 8 |
| Oleol Alcohol + 10% Kraton ® 1107 | 4 |
| 5. Isopropyl Palmitate | 7 |
| Ispropyl Palmitate + 10% Kraton ® 1107 | 6 |
| 6. Drakeol ™ #35 | 10 |
| Drakeol ™ #35 + 2% Kraton ® 1107 | 7 |
| 7. Peanut Oil | 11 |
| Peanut oil + 2% Kraton ® 1107 | 7 |
| 8. Acetulan ™ | 7 |
| Acetulan ™ + 2% Kraton ® 1107 | 5 |
| 9. Polylan ™ | 5 |
| Polylan ™ + 10% Kraton ® 1107 | 4 |
| 10. Dibutyl Phthalate | 12 |
| Dibutyl Phthalate + 10% Kraton ® 1107 | 5.5 |
| 11. Diisopropyl Adipate | 10 |
| Diisopropyl Adipate + 10% Kraton ® 1107 | 6 |
| 12. Dibutyl Sebacate | 6 |
| Dibutyl Sebacate + 10% Kraton ® 1107 | 4 |
| 13. Butyl Stearate | 7 |
| Butyl Stearate + 10% Kraton ® 1107 | 3 |
| 14. Robane ™ | 6 |
| Robane ™ + 10% Kraton ® 1107 | 4 |

Table II compares the lubricity of the composition of Example 1 with shaving creams that have been commercially available. Commercially available shaving creams are less slippery that Example 1 even immediately after application to the test surface. Immediate measurement of the angle after application is the Initial Inclined Plane Slipperiness Test Angle. As time goes on, Example 1 sustains its lubricity, while commercially available shaving creams become much less slippery, or virtually dry out altogether. Preferably, the shaving preparation of this invention has an Inclined Plane Slipperiness Test Angle after 4 minutes that is not more than about 10% higher than the Initial Inclined Plane Slipperiness Test Angle.

TABLE II

INCLINE PLANE SLIPPERINESS TEST OF SHAVING CREAMS

| | Angle in Degrees | |
|---|---|---|
| Shaving Cream | Initial | After 4 Minutes |
| 1. Barbasol ™ (Pfizer) | 7 | Too dry, powdery |
| 2. Colgate ™ (Colgate-Palmolive) | 9 | Too dry, powdery |
| 3. Old Spice ™ (Scholten) | 8 | Too dry, powdery |
| 4. Foamy ™ Surf-Spray ™ (Gillette) | 10 | 15 |
| 5. Foamy ™ Regular (Gillette) | 7 | 13 |
| 6. Example 1 | 6 | 6 |

We claim:

1. A shaving preparation suitable for application to human or animal skin comprising at least 5% by weight of an emollient oil, a water insoluble thermoplastic polymeric elastomer additive in a weight ratio of emollient oil to additive of between about 5:1 and 20:1, and at least 5% by weight of soap, detergent or a combination thereof.

2. A shaving preparation of claim 1 wherein said emollient oil and water insoluble thermoplastic polymeric elastomer additive are provided in a weight ratio of between about 8:1 and 10:1.

3. A shaving cream preparation of claim 1 comprising
  a) 5-30% of an emollient oil,
  b) a water insoluble thermoplastic polymeric elastomer additive present in a ratio of emollient oil to additive of between about 5:1 and 20:1, and
  c) at least 5% by weight of soap, detergent or a combination thereof.

4. A shaving cream preparation of claim 3 comprising
  a) 5-30% of an emollient oil,
  b) a water insoluble thermoplastic polymeric elastomer additive present in a ratio of emollient oil to additive of between about 5:1 and 20:1, and
  c) between 10 and 50% by weight of soap, detergent or a combination thereof.

5. A shaving cream preparation of claim 4 comprising
  a) 5-30% of an emollient oil,
  b) a water insoluble thermoplastic polymeric elastomer additive present in a ratio of emollient oil to additive of between about 5:1 and 20:1, and
  c) between 15 and 30% by weight of soap, detergent or a combination thereof.

6. The shaving preparation of claim 1, wherein said water insoluble thermoplastic polymeric elastomer additive is a multi-block copolymer comprising block A and block B; wherein block A is made from a monomer wherein the corresponding homopolymer has a $T_g$ less than about 10° C., and block B is made from a monomer wherein the corresponding homopolymer has a $T_g$ greater than about 90° C.; said block B is about 15–40% by weight of the total thermoplastic polymeric elastomer additive.

7. The shaving preparation of claim 6, wherein said water insoluble thermoplastic polymeric elastomer additive is a two-block copolymer.

8. The shaving preparation of claim 7, wherein said water insoluble thermoplastic polymeric elastomer additive is a styrene-butadiene copolymer.

9. The shaving preparation of claim 6, wherein said water insoluble thermoplastic polymeric elastomer additive is a tri-block copolymer.

10. The shaving preparation of claim 9, wherein said water insoluble thermoplastic polymeric elastomer additive is a styrene-isoprene-styrene copolymer.

11. The shaving preparation of claim 9, wherein said water insoluble thermoplastic polymeric elastomer additive is a styrene-butadiene-styrene copolymer.

12. The shaving preparation of claim 9, wherein said water insoluble thermoplastic polymeric elastomer additive is a styrene-ethylene/butylene-styrene copolymer.

13. The shaving preparation of claim 3, wherein said water insoluble thermoplastic polymeric elastomer additive comprises between about 1 and 5% by weight of the total preparation.

14. The shaving preparation of claim 13, wherein said water insoluble thermoplastic polymeric elastomer additive comprises between about 2 and 4% by weight of the total preparation.

15. The shaving preparation of claim 3, wherein said soap is a mixture of salts of stearic acid.

16. The shaving preparation of claim 1, wherein said preparation has an initial Inclined Plane Slipperiness Test Angle that is less than about 70% of the Inclined Plane Slipperiness Test Angle of the same composition not containing water insoluble thermoplastic polymeric elastomer additive.

17. The shaving preparation of claim 1, wherein said preparation has an Inclined Plane Slipperiness Test Angle after 4 minutes that is not more than about 10% higher than the Initial Inclined Plane Slipperiness Test Angle.

18. A method of preparing a hairy area of an animal or human for shaving comprising applying the shaving preparation of claim 1 to the hairy area in an amount effective to lubricate and moisturize the area to be shaved.

* * * * *